(12) United States Patent
Kim et al.

(10) Patent No.: US 8,727,999 B2
(45) Date of Patent: May 20, 2014

(54) PULSE MEASUREMENT DEVICE, METHOD AND MEDIUM CONTROLLING SENSOR ACCORDING TO EXERCISE ACTIVITY LEVEL

(75) Inventors: Youn Ho Kim, Yongin-si (KR); Kun Soo Shin, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1552 days.

(21) Appl. No.: 11/783,055

(22) Filed: Apr. 5, 2007

(65) Prior Publication Data

US 2007/0244399 A1 Oct. 18, 2007

(30) Foreign Application Priority Data

Apr. 17, 2006 (KR) .................. 10-2006-0034429

(51) Int. Cl.
*A61B 5/02* (2006.01)
(52) U.S. Cl.
USPC ............................. 600/500; 600/493; 600/494
(58) Field of Classification Search
USPC .................................. 600/323–340, 500–503
See application file for complete search history.

(56) References Cited

U.S. PATENT DOCUMENTS

| | | | |
|---|---|---|---|
| 6,120,459 A | 9/2000 | Nitzan et al. | |
| 6,513,532 B2 * | 2/2003 | Mault et al. | 600/595 |
| 6,606,509 B2 | 8/2003 | Schmitt | |
| 6,699,199 B2 | 3/2004 | Asada et al. | |
| 2007/0055163 A1 * | 3/2007 | Asada et al. | 600/485 |

FOREIGN PATENT DOCUMENTS

| | | |
|---|---|---|
| JP | 2003-199719 | 7/2003 |
| WO | WO 2005051184 A1 * | 6/2005 |

* cited by examiner

*Primary Examiner* — Michael Kahelin
*Assistant Examiner* — Eric Messersmith
(74) *Attorney, Agent, or Firm* — Staas & Halsey LLP (57) ABSTRACT

A pulse measurement device for more precisely measuring a pulse, including a sensing unit to sense a photoplethysmography (PPG) signal and an acceleration signal obtained from a user, a pressure control unit to control pressure applied to the sensing unit, and a signal determination unit to determine an optimum pressure range by analyzing the PPG signal varying with a change of the pressure applied to the sensing unit by the pressure control unit and to determine an exercise level of the user by using the acceleration signal.

11 Claims, 11 Drawing Sheets

PULSE MEASUREMENT DEVICE, METHOD AND MEDIUM CONTROLLING SENSOR ACCORDING TO EXERCISE ACTIVITY LEVEL

CROSS-REFERENCE TO RELATED APPLICATIONS

This application claims priority from Korean Patent Application No. 10-2006-0034429, filed on Apr. 17, 2006, in the Korean Intellectual Property Office, the disclosure of which is incorporated herein by reference.

BACKGROUND

1. Field

An embodiment of the present invention relates to a pulse measurement device, method and medium, and more particularly, to a device, method and medium measuring a pulse by controlling pressure applied to a photoplethysmography (PPG) sensor and an amount of light applied to a PPG sensor according to an exercise activity level of a user.

2. Description of the Related Art

Recently, due to a heightened awareness of fitness, a growing number of people are now concerned with living a healthy lifestyle. Adequate nutrition and frequent exercise are known to be a necessary component of the healthy lifestyle. However, when a person excessively exercises without consideration for his or her body condition, problems may occur.

Accordingly, an exercise management method that assists a user in maintaining the appropriate level of exercise for the user's current fitness level is needed. A method of recognizing and managing an exercise state of the user by measuring a bio-signal such as a pulse rate or a heart rate is a representative example.

In this regard, a photoplethysmograph (PPG) is a device that detects the perfusion of blood through tissue by shining light through it. PPG works by shining infrared light through a capillary bed. As arterial pulsations fill the capillary bed, the changes in volume of the vessels modify the absoption, reflection, and scattering of the light. Although PPG accurately indicates the timing of events such as heart rate, it is sensitive to motion artifacts.

In a conventional pulse measurement method using a PPG signal, a pulse rate before exercise and a pulse rate after exercise are measured and compared with each other. This makes continuous or real-time analysis impossible.

Another conventional pulse measurement method uses an electrocardiogram (EKG). Since several electrodes are attached to the chest of a user using a chest-band to measure the EKG, it is similarly inconvenient and impracticable to analyze data in real-time.

Figure 1A:
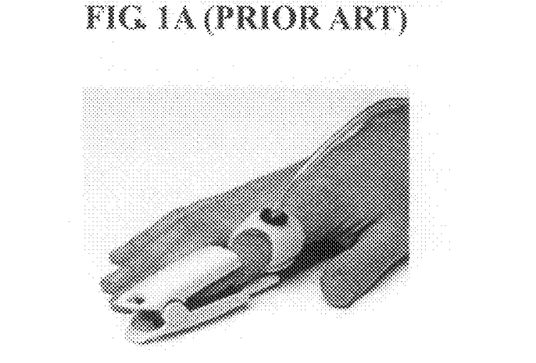
FIGS. 1A, 1B, and 1C illustrate examples of a conventional PPG measurement method.
Figure 1B:
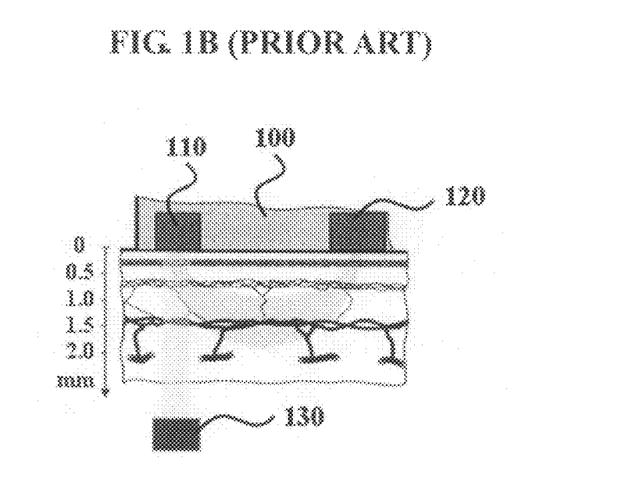
Figure 1C:
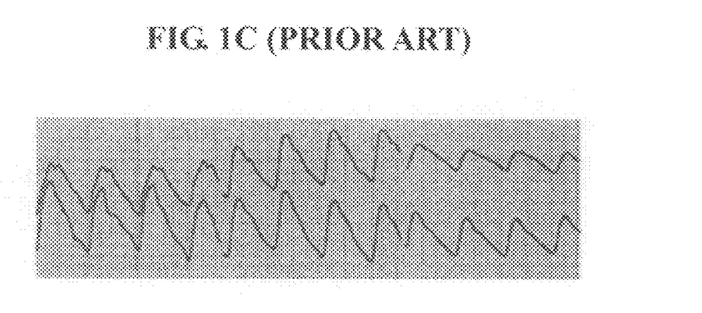

Generally, in the conventional PPG measurement method, as shown in FIG. 1A, a measurement device is attached to bare skin such as on an end of a finger or toe of a user. Infrared light is generated by an LED 110, which is a light source of a probe 100, as shown in FIG. 1B. There, a first light sensor 120 senses an amount of light reflected after penetrating the skin and being absorbed into erythrocytes flowing in a blood vessel. A second light sensor 130 senses the amount of infrared light penetrating the blood vessel. The detected light appears as waves as shown in FIG. 1C, and whether the blood circulates well is determined by analyzing the detected waves.

Figure 2:
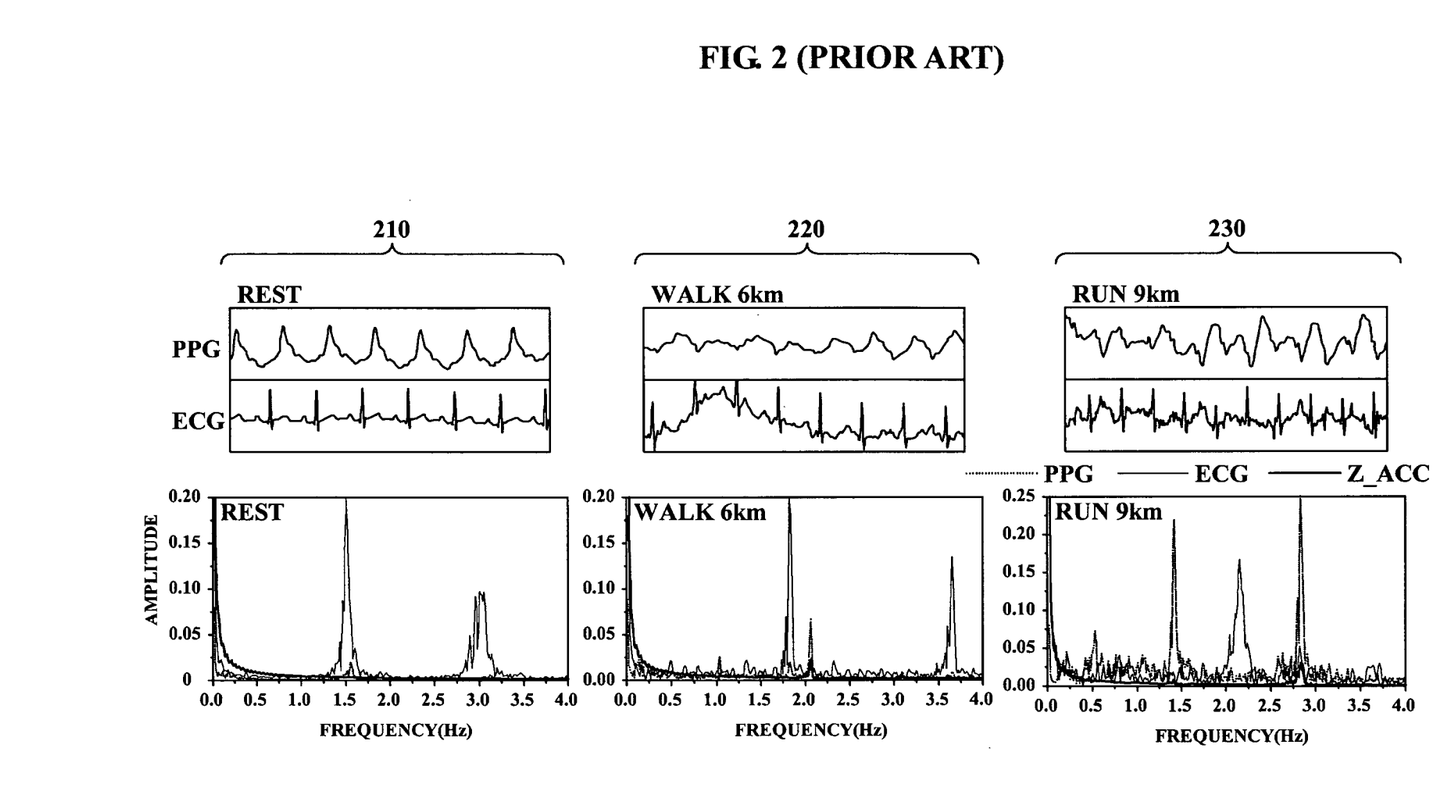
FIG. 2 illustrates a change of a signal according to an exercise state of a user.

As shown in FIG. 2, a peak of a PPG signal in a rest state 210 is continually generated, while having a slight delay from an R-peak of an EKG signal, and has the same frequency component in a fast Fourier transform. As shown in FIG. 2, the generated EKG signal and the generated PPG signal are the same in the rest state 210, which includes a resting state and a walking state of up to 3 km per hour.

However, in a walking state 220 at a speed of 6 km per hour or a running state 230 at a speed of 9 km per hour, the frequency of the PPG signal is consistent with a frequency Z_ACC generated by an acceleration sensor rather than a frequency of the EKG signal, as shown in FIG. 2.

As described above, because the conventional PPG sensor is increasingly affected by the activity level of the user, as the user activity level increases, the frequency of the detected PPG signal becomes more consistent with the frequency of the acceleration signal.

Figure 3:
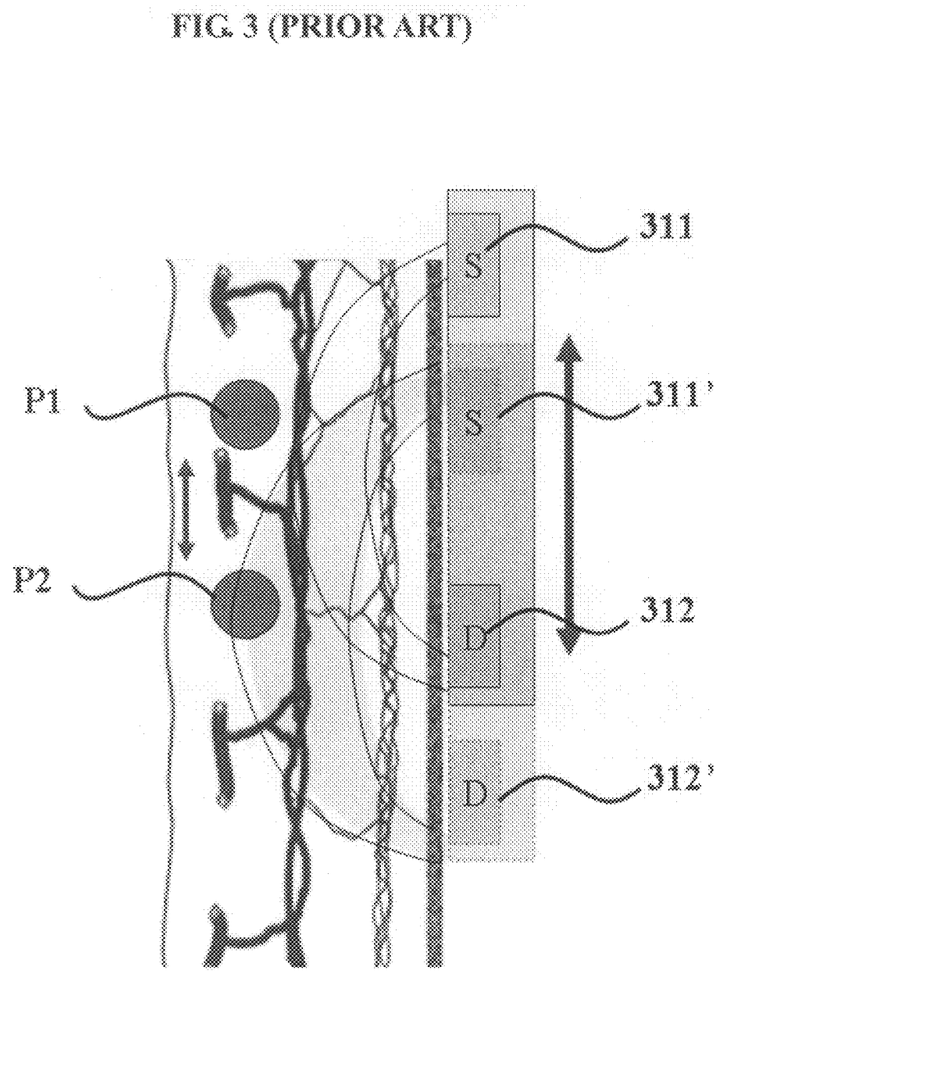
FIG. 3 illustrates an example of a change of a conventional measurement point.

In addition, referring to FIG. 3, as a measurement point is changed from a first point P1 to a second point P2, corresponding to the change in position of sensors S and D from 311 and 312 to 311' and 312' respectively, a PPG signal can no longer be detected reliably.

Figure 4:
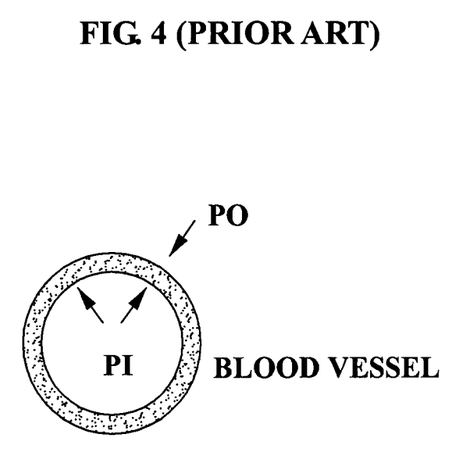
FIG. 4 illustrates blood vessel pressure.

Generally, as shown in FIG. 4, when measuring a pulse, since a maximum peak value of a PPG signal is generated at a point (Pt=Pi−Po=0) in which inner pressure Pi of a blood vessel is identical with external pressure Po of the blood vessel, with the external pressure Po being an optimum pressure 510 for sensing the PPG signal.

Figure 5:
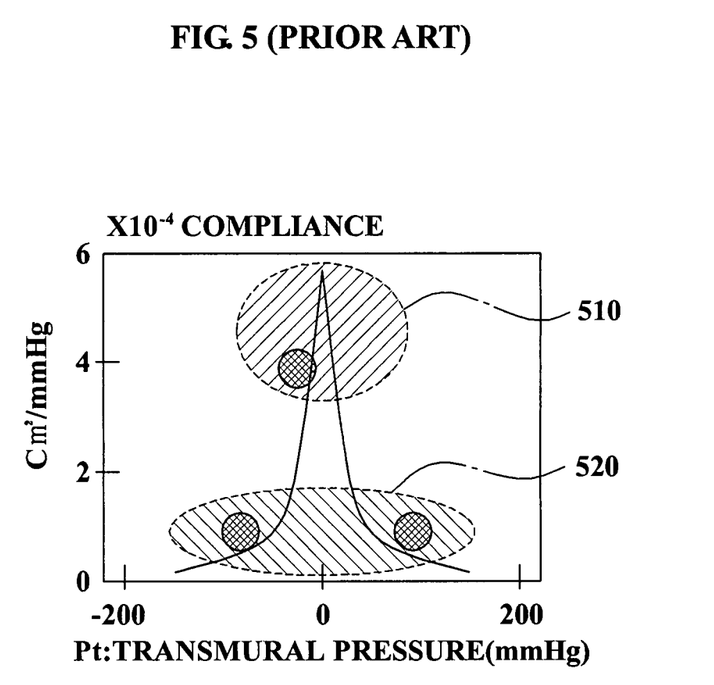
FIG. 5 illustrates a conventional measured pressure change and optimum pressure according to user activity.

Referring to FIG. 5, in the conventional PPG sensor, the optimum PPG measurement pressure point changes from points/areas 510 to 520 due to instability of a sensor position as movement increases with the user's increased activity. This makes detecting a clear PPG signal difficult.

Accordingly, since noise and interfering light, generated when a user exercises, interferes with the precise measuring of a pulse, a technology for measuring a pulse by stably detecting a PPG signal is desired.

SUMMARY

An aspect of the present invention provides a device, method and medium measuring a pulse by detecting a PPG signal while a user exercises.

An aspect of the present invention also provides a device, method and medium more precisely measuring a pulse by detecting a PPG signal by automatically controlling pressure of a PPG sensor according to an activity level of a user.

An aspect of the present invention also provides a device, method and medium more precisely measuring a pulse by compensating for a weak PPG signal by increasing an amount of light when the weak signal is generated due to excessive pressurization of a PPG sensor.

Additional aspects and/or advantages of the invention will be set forth in part in the description which follows and, in part, will be apparent from the description, or may be learned by practice of the invention.

According to an aspect of the present invention, there is provided a pulse measurement device including a sensing unit to sense a photoplethysmography (PPG) signal and an acceleration signal obtained from a user, a pressure control unit to control pressure applied to the sensing unit, and a signal determination unit to determine an optimum pressure range by analyzing the PPG signal varying with a change of the pressure applied to the sensing unit by the pressure control unit and to determine an exercise level of the user by using the acceleration signal.

According to another aspect of the present invention, there is provided a pulse measurement method including establishing an optimum pressure range of a PPG sensor by changing pressure applied to the PPG sensor and analyzing a PPG signal detected by the PPG sensor, measuring an exercise level of a user by analyzing an acceleration signal detected by an acceleration sensor, controlling the pressure applied to the PPG sensor based on the optimum pressure range according to the exercise level of the user, and measuring a pulse by analyzing the PPG signal detected by the PPG sensor to which the controlled pressure is given.

According to another aspect of the present invention, there is provided at least one medium comprising computer readable code to control at least one processing element to implement a pulse measurement method, the method including establishing an optimum pressure range of a PPG sensor by changing pressure applied to the PPG sensor and analyzing a PPG signal detected by the PPG sensor, measuring an exercise level of a user by analyzing an acceleration signal detected by an acceleration sensor, controlling the pressure applied to the PPG sensor based on the optimum pressure range according to the exercise level of the user, and measuring a pulse by analyzing the PPG signal detected by the PPG sensor to which the controlled pressure is given.

According to another aspect of the present invention, there is provided a pulse measurement device including a sensing unit to sense a PPG signal and an acceleration signal obtained from a user, a pressure control unit to control pressure applied to the sensing unit, and a signal determination unit to direct the pressure control unit to vary the pressure applied to the sensing unit based on the acceleration signal obtained from the user.

BRIEF DESCRIPTION OF THE DRAWINGS

These and/or other aspects and advantages of the present invention will become apparent and more readily appreciated from the following description of embodiments, taken in conjunction with the accompanying drawings of which.

DETAILED DESCRIPTION OF EMBODIMENTS

Reference will now be made in detail to one or more embodiments of the present invention, examples of which are illustrated in the accompanying drawings, wherein like reference numerals refer to like elements throughout. It should be noted that the present invention may be embodied in many different forms/ways and should not be construed as being limited to embodiments set forth herein. Embodiments are described below to explain the present invention by referring to the figures.

Figure 6:
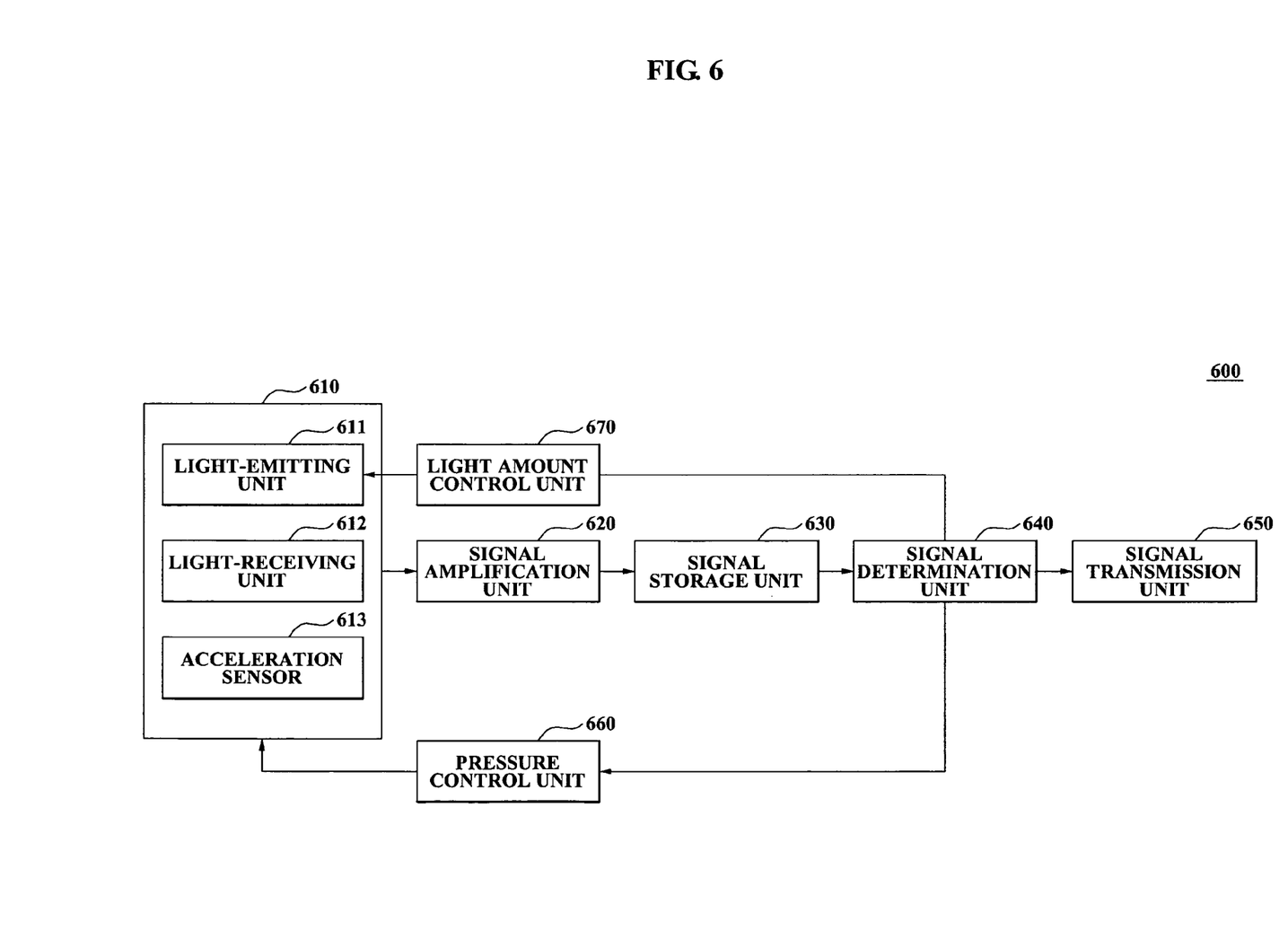
FIG. 6 illustrates a pulse measurement device, according to one or more embodiments of the present invention.

FIG. 6 illustrates a pulse measurement device 600 according to one or more embodiments of the present invention.

Referring to FIG. 6, the pulse measurement device 600 may include a sensing unit 610, a signal amplification unit 620, a signal storage unit 630, a signal determination unit 640, a signal transmission unit 650, a pressure control unit 660, and a light amount control unit 670, for example.

The sensing unit 610 may sense a PPG signal and an acceleration signal obtained from a user. The sensing unit 610 may include a light-emitting unit 611, e.g., a PPG sensor for sensing the PPG signal, a light-receiving unit 612, and an acceleration sensor 613 for sensing the acceleration signal.

Accordingly, the light-emitting unit 611 may generate and irradiate an infrared ray to the skin of the user, such that the light-receiving unit 612 receives light of the infrared ray irradiated to the skin, absorbed into erythrocytes and reflected from the erythrocytes, and, for example, detects a PPG signal.

The pressure control unit 660 may control pressure applied to the sensing unit 610.

Figure 7:
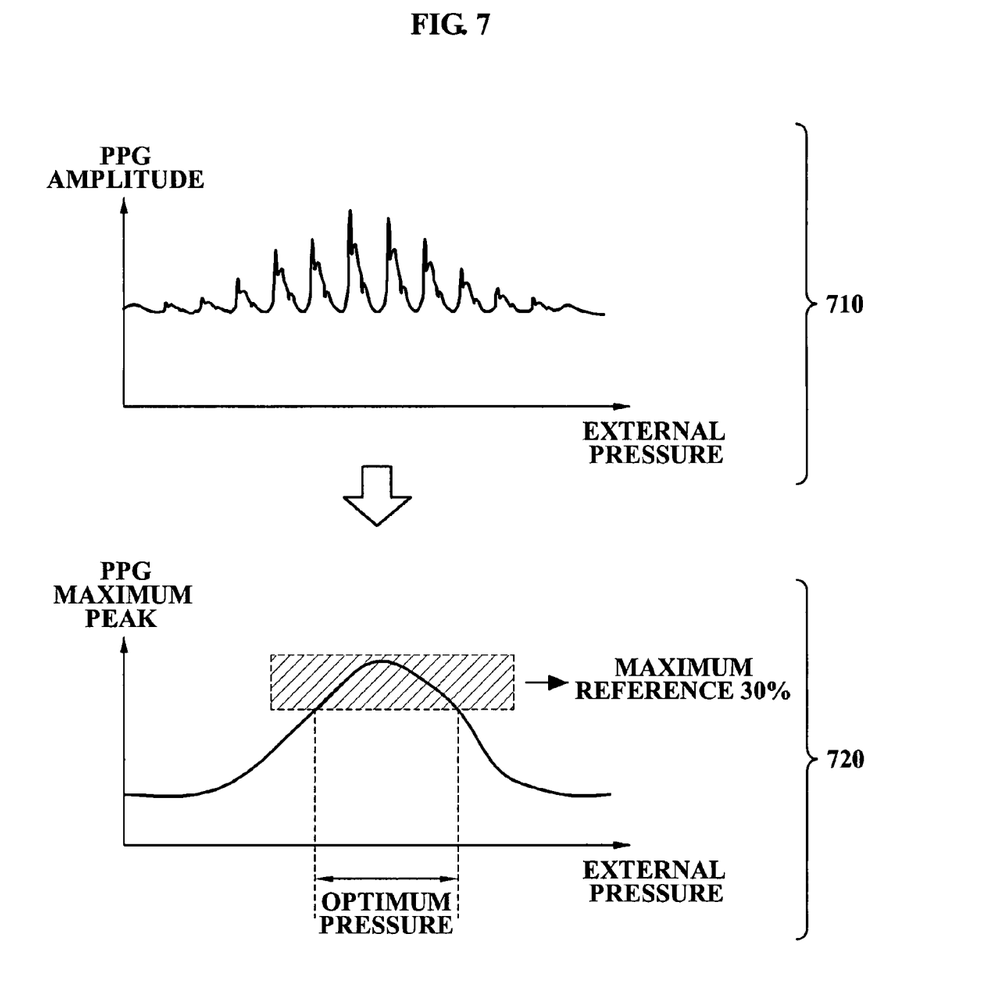
FIG. 7 illustrates a change of a detected PPG signal corresponding to an increase of pressure applied to a sensing unit, according to one or more embodiments of the present invention.

FIG. 7 illustrates a change in the detected PPG signal corresponding to an increase of the pressure applied to the sensing unit 610. Referring to FIG. 7, a first graph 710 illustrates a change in amplitude of the PPG signal corresponding to a change of the pressure applied to the sensing unit 610, and a second graph 720 illustrates a change of a maximum peak of the PPG signal corresponding to the change in the external pressure. When the external pressure increases, the amplitude of the PPG signal increases to a certain range, and then decreases, as shown in graph 710. Namely, as shown in graph 720, when the external pressure increases, the maximum peak of the PPG signal does not unconditionally increase but begins to decrease when the external pressure increases beyond a certain level. Here, optimum pressure indicates external pressure corresponding to a range within 30% of a maximum value of the maximum peak, as shown in the second graph 720. Within this range, the PPG sensor can stably detect the PPG signal.

The acceleration sensor 613 may detect an acceleration signal corresponding to an exercise level of the user, for example.

Figure 8:
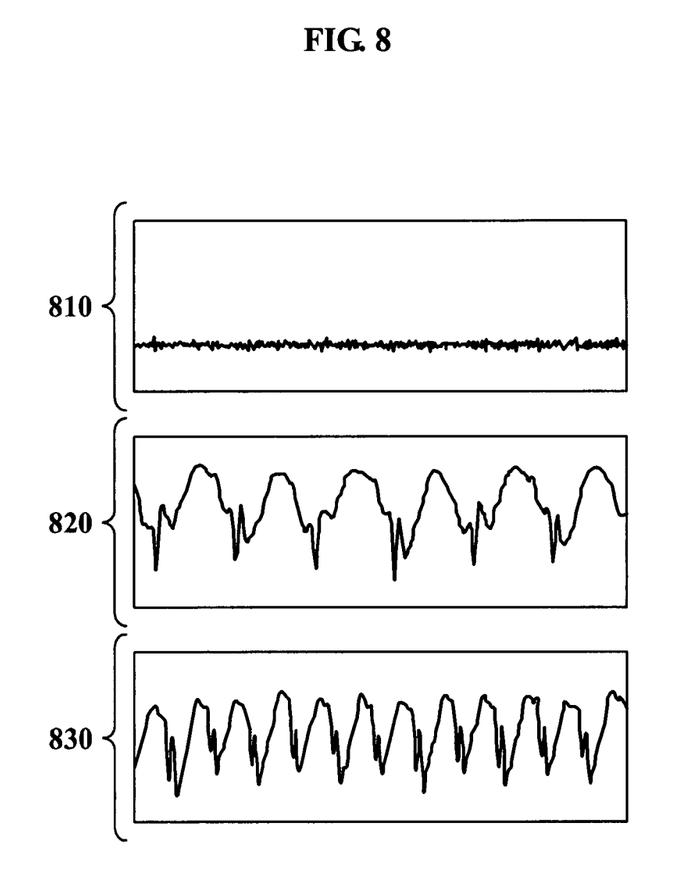
FIG. 8 illustrates an acceleration signal detected by an acceleration sensor, corresponding to an exercise state of a user, according to one or more embodiments of the present invention.

FIG. 8 illustrates an acceleration signal detected by an acceleration sensor, corresponding to an exercise state of a user. Referring to FIG. 8, an acceleration signal 810 may indicate a signal detected by the acceleration sensor 613 when the exercise state of the user is a rest state. Another acceleration signal 820 may indicate a signal detected by the acceleration sensor 613 when the exercise state of the user is light exercise such as walking. Still another acceleration signal 830 may indicate a signal detected by the acceleration sensor 613 when the exercise state of the user is heavy exercise such as running. Accordingly, the pulse measurement device 600 according to one or more embodiments of the present invention may determine the exercise state of the user by analyzing an acceleration signal detected by the acceleration sensor 613.

In an embodiment, the signal amplification unit 620 may amplify the PPG signal detected by the light-receiving unit 612. The signal amplification unit 620 may also amplify the detected acceleration signal.

Here, the signal storage unit 630 may store the amplified PPG signal or the amplified acceleration signal.

The signal determination unit 640 may determine an optimum pressure range by analyzing the PPG signal varying with the change of the pressure applied to the sensing unit 610, and may determine the exercise amount of the user using the acceleration signal. Namely, the signal determination unit 640 may determine the optimum pressure range suitable for the user by analyzing the maximum peak of the detected PPG signal varying with the change of the pressure applied to the sensing unit, as shown, for example, in FIG. 9.

Figure 9:
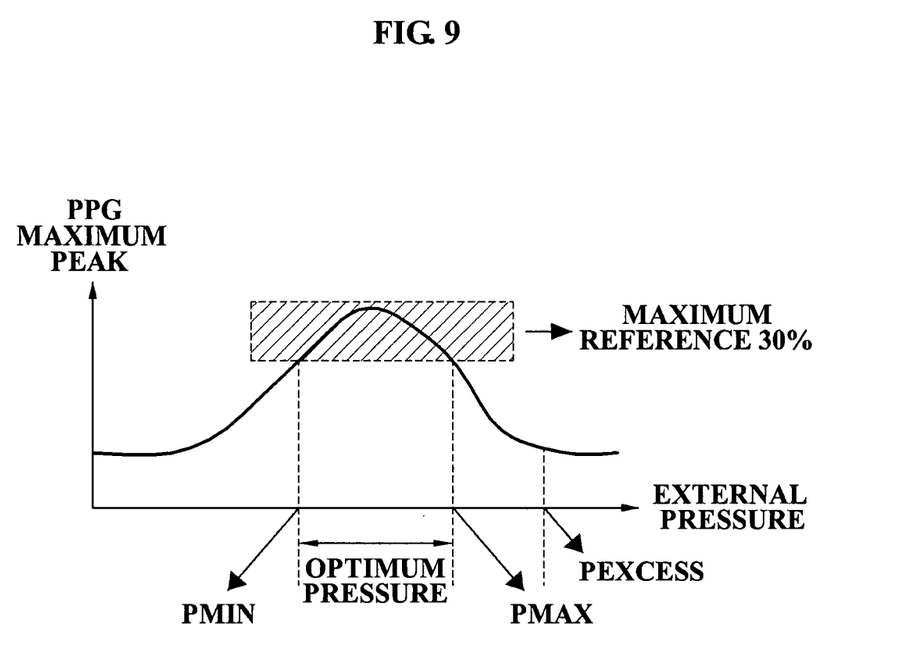
FIG. 9 illustrates an example of varying pressure corresponding to the exercise state of the user, according to one or more embodiments of the present invention.

FIG. 9 illustrates an example of varying external pressure applied to the sensing unit according to an exercise state of the user.

Referring to FIG. 9, an optimum pressure range may include a pressure range corresponding to a range determined based on a maximum peak value of a PPG signal. The optimum pressure range is an external pressure range corresponding to the range determined based on the maximum peak value, because the peak value of the PPG signal is greatest when an inner pressure of a blood vessel is identical with the external pressure of the blood vessel. The optimum pressure range may include external pressure corresponding to a range within 30% based on the maximum peak value of the PPG signal. For example, when the peak value of the PPG signal is 100 for the external pressure, the optimum pressure range may be from 70 to 100 where 70 is the minimum pressure Pmin and 100 is the maximum pressure Pmax.

The minimum pressure Pmin is the external pressure applied to the sensing unit 610 when the exercise amount of the user is determined to correspond to a rest state, and the maximum pressure Pmax is the external pressure applied to the sensing unit 610 when the exercise amount of the user is determined to correspond to a walking state, for example. Excessive pressure Pexcess is greater than the maximum pressure and is applied to the sensing unit 610 when the exercise amount of the user is determined to correspond to a running state, for example.

The signal determination unit 640 may determine an exercise amount of the user by analyzing the acceleration signal. The signal determination unit 640 may further control the pressure control unit 660 to vary the pressure applied to the sensing unit 610 corresponding to the determined exercise amount of the user.

When the acceleration signal is similar to the acceleration signal 810, the signal determination unit 640 may determine the exercise amount of the user to be a rest state. The signal determination unit 640 may further direct the pressure control unit 660 to control the pressure applied to the sensing unit 610 to be the minimum pressure, Pmin, of the optimum pressure range suitable for the rest state.

When the acceleration signal is similar to the acceleration signal 820, the signal determination unit 640 may determine the exercise amount of the user to be a walking state. The signal determination unit 640 may further control the pressure control unit 660 to control the pressure applied to the sensing unit 610 to be the maximum pressure, Pmax, of the optimum pressure range suitable for the walking state.

When the acceleration signal is the acceleration signal 830, the signal determination unit 640 may determine the exercise amount of the user to be a running state. The signal determination unit 640 may further control the pressure control unit 660 to control the pressure applied to the sensing unit 610 to be the excessive pressure, Pexcess, over the optimum pressure range suitable for the walking state. Also, the signal determination unit 640 may control the light amount control unit 670 to increase an amount of incident light on the light-emitting unit 611 to prevent a PPG signal from becoming weaker when the excessive pressure Pexcess is applied to the sensing unit 610.

The signal determination unit 640 may calculate a pulse of the user by analyzing the PPG signal detected by the light-receiving unit 612, of the sensing unit 610, whose pressure or light amount is controlled based on the optimum pressure range.

The signal transmission unit 650 may forward data including the calculated pulse, or the exercise amount of the user, to an apparatus monitoring the condition of the user, for example. The signal transmission unit 650 may forward the data including the calculated pulse or the exercise amount of the user to the apparatus monitoring the user's condition, continuously, or in real time.

The pressure control unit 660 may control the pressure applied to the sensing unit 610 based on the optimum pressure range according to the exercise amount of the user, as determined by the signal determination unit 640.

The pressure control unit 660 may maintain the pressure applied to the sensing unit 610 at the minimum pressure, Pmin, of the optimum pressure range when the exercise amount of the user is determined to correspond to the rest state by the signal determination unit 640. Since the movement of the user is not significant in the rest state, the sensing unit 610 may stably detect the PPG signal even though the pressure applied to the sensing unit 610 is not great.

As described above, when the user rests, the pulse measurement device 600, according to one or more embodiments of the present invention, may increase user convenience and stably detect the PPG signal by establishing the pressure applied to the sensing unit 610 to be at a low pressure, i.e., the minimum pressure Pmin of the optimum pressure range.

Also, when the exercise amount of the user is determined to correspond to the walking state by the signal determination unit 640, the pressure control unit 660 may maintain the pressure applied to the sensing unit 610 at the maximum pressure, Pmax, of the optimum pressure range.

When the exercise amount of the user corresponds to the walking state, greater pressure must be applied to the sensing unit 610 than in the rest state. This is because the user's movement is greater than in the rest state. Nevertheless, the pulse measurement device 600, according to one or more embodiments of the present invention, may precisely measure the user's pulse by detecting the PPG signal. This is because the increased pressure results in a PPG signal that is clearer and less affected by the movement.

Also, when the exercise amount of the user is determined to correspond to the running state by the signal determination unit 640, the pressure control unit 660 may maintain the pressure applied to the sensing unit 610 at greater than the optimum pressure range, according to the control of the signal determination unit 640.

As described above, when the exercise amount of the user corresponds to a running state, pressure greater than the optimum pressure range may be applied to the sensing unit 610. Due to this pressure, the pulse measurement device 600 may be less affected by the movement.

The light amount control unit 670 may control the amount of incident light on the light-emitting unit 611. Namely, when the exercise amount of the user is determined to correspond to the running state by the signal determination unit 640, the light amount control unit 670 may increase the incident light on the light-emitting unit 611.

As described above, the pulse measurement device 600 may reduce energy consumption by selectively controlling the amount of light of the light-emitting unit 611. The incident light may only be increased during heavy exercise, as detected using the detected acceleration signal.

Figure 10:
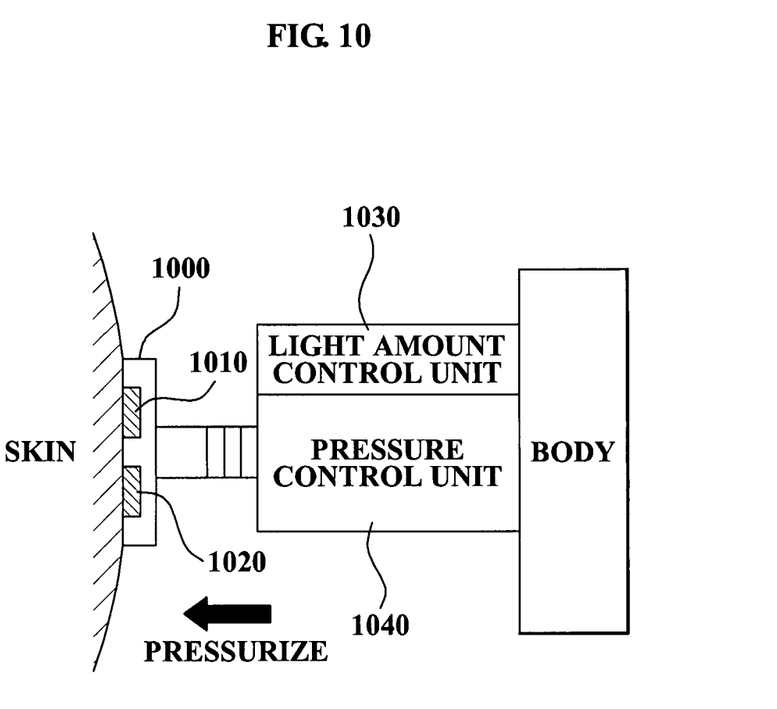
FIG. 10 illustrates a PPG sensor, a pressure control unit, and a light amount control unit of the PPG sensor, according to one or more embodiments of the present invention.

FIG. 10 illustrates an arrangement of a PPG sensor 1000, a pressure control unit 1040, and a light amount control unit 1030 of the PPG sensor 1000.

Referring to FIG. 10, the PPG sensor 1000 may include a light-emitting unit 1010 and a light-receiving unit 1020. The light-emitting unit 1010 emits a certain amount of light to the skin of a user, and the light-receiving unit 1020 detects a PPG signal by receiving light reflected by the skin.

The light amount control unit 1030 may be embodied as a light amplifier, and control the amount of light emitted by the light-emitting unit 1010, for example. Therefore, in the PPG sensor 1000, an amount of incident light on the light-emitting unit 1010 may be controlled by the light amount control unit 1030, and a PPG signal according to the controlled amount of incident light may be detected.

The pressure control unit 1040 may be embodied as a motor drive or an air pump, for example, and may control pressure applied to the PPG sensor 1000 by controlling the motor drive or the air pump, according to the determined exercise amount of a user.

For example, when the determined exercise amount of the user corresponds to a rest state, the pressure control unit 1040 may control the pressure applied to the PPG sensor 1000 to be a minimum pressure of the optimum pressure range. When the determined exercise amount of the user corresponds to a walking state, the pressure control unit 1040 may control the pressure applied to the PPG sensor 1000 to be a maximum pressure of the optimum pressure range. When the determined exercise amount of the user corresponds to a running state, the pressure control unit 1040 may control the pressure applied to the PPG sensor 1000 to be a pressure greater than the optimum pressure range. To prevent the amplitude of a signal from the PPG sensor from decreasing because the pressure applied to the PPG sensor 1000 is over the optimum pressure range when the exercise amount corresponds to the running state, the light amount control unit 1030 may direct the amount of light of the light-emitting unit 1010 so as to increase the amount of incident light.

Accordingly, the pulse measurement device according to one or more embodiments of the present invention may control pressure applied to a PPG sensor at a suitable level, according to an exercise amount of a user, and stably detect a PPG signal by controlling an amount of incident light, thereby precisely measuring a pulse.

Figure 11:
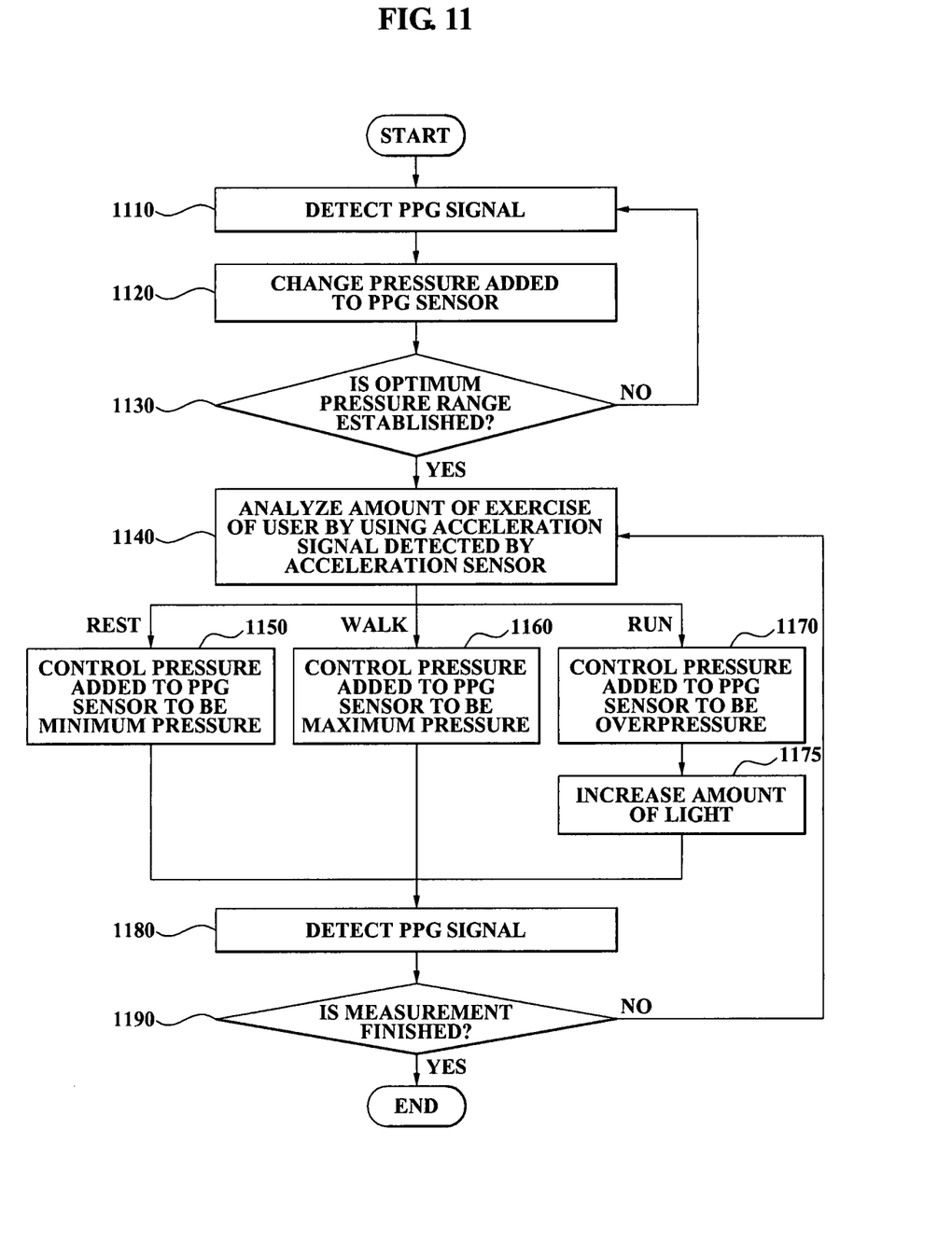
FIG. 11 illustrates a pulse measurement method, according to one or more embodiments of the present invention.

FIG. 11 illustrates a pulse measurement method, according to an embodiment of the present invention.

Referring to FIG. 11, in operation 1110, a PPG signal may be detected, e.g., using a PPG sensor.

In operation 1120, pressure applied to the PPG sensor may be changed, e.g., using a motor or an air pump coupled with the PPG sensor. For example, the pulse measurement device may increase the pressure applied to the PPG sensor using the motor or the air pump.

In operation 1130, it may be determined whether an optimum pressure range for stably detecting the PPG signal has been established. For example, the optimum pressure range may be a pressure range determined from a maximum peak value of the detected PPG signal, according to the change of the pressure applied to the PPG sensor.

When the optimum pressure range is not established, the pulse measurement device may establish the optimum pressure range according to the change in pressure applied to the PPG sensor, by again performing the described operation 1110.

As described above, the pulse measurement method, according to one or more embodiments of the present invention, may establish an optimum pressure range. The optimum pressure range may be established by analyzing the PPG signal detected by the PPG sensor according to the change in pressure applied to the PPG sensor by performing operations 1110 through 1130.

When the optimum pressure range is established, in operation 1140, the pulse measurement device may detect an acceleration signal according to an exercise amount of a user using an acceleration sensor, and may analyze whether the exercise amount of the user corresponds to a rest state, a walking state, or a running state, for example, using the detected acceleration signal.

For example, when the acceleration signal detected by the acceleration sensor is the acceleration signal 810 shown in FIG. 8, the pulse measurement device may determine the exercise amount of the user to correspond to the rest state. When the acceleration signal detected by the acceleration sensor is the acceleration signal 820 shown in FIG. 8, the pulse measurement device may determine the exercise amount of the user to correspond to the walking state. When the acceleration signal detected by the acceleration sensor is the acceleration signal 830 shown in FIG. 8, the pulse measurement device may determine the exercise amount of the user to correspond to the running state.

As described above, in operation 1140, the pulse measurement device may measure the exercise amount of the user by analyzing the acceleration signal detected by the acceleration sensor.

In an embodiment, when the exercise amount of the user corresponds to the rest state, in operation 1150, the pulse measurement device may control the pressure applied to the PPG sensor to be a minimum pressure, Pmin, of the optimum pressure range shown in FIG. 9.

In a further embodiment, when the exercise amount of the user corresponds to the walking state, in operation 1160, the pulse measurement device may control the pressure applied to the PPG sensor to be a maximum pressure, Pmax, of the optimum pressure range shown in FIG. 9.

Still further, when the exercise amount of the user corresponds to the running state, in operation 1170, the pulse measurement device may control the pressure applied to the PPG sensor to be an excessive pressure, Pexcess, greater than the optimum pressure range shown in FIG. 9.

When the excessive pressure Pexcess is applied to the PPG sensor, a maximum peak value of the PPG signal detected by the PPG sensor may be decreased even though a measurement position of the PPG sensor is stable. The pulse measurement device may increase an amount of light of the PPG sensor to increase an amount of incident light on the PPG sensor in operation 1175 to possibly offset this decrease.

As described above, in the pulse measurement method, according to one or more embodiments of the present invention, the amount of light may be selectively increased, for example, only when the user heavily exercises as in running, thereby reducing unnecessary current consumption.

The pulse measurement device, according to an embodiment of the present invention, may control the pressure applied to the PPG sensor, and the amount of light of the PPG sensor based on the optimum pressure range, according to the determined exercise amount of the user via operations 1150 through 1175, and thereby stably detect the PPG signal.

In operation 1180, the pulse measurement device may detect the PPG signal using the PPG sensor, whose pressure or amount of light is controlled, and may measure a pulse of the user.

For example, when the exercise amount of the user corresponds to the rest state, the pulse measurement device may detect the PPG signal using the PPG sensor. There, the pressure applied to the PPG sensor is controlled to be the minimum pressure Pmin of the optimum pressure range. The pulse measurement device further may measure the pulse when the exercise amount of the user corresponds to the rest state by analyzing the detected PPG signal.

For example, when the exercise amount of the user corresponds to the walking state, the pulse measurement device may detect the PPG signal using the PPG sensor. The pressure applied to the PPG sensor may be controlled to be the maximum pressure Pmax of the optimum pressure range. The pulse measurement device may further measure the pulse when the exercise amount of the user corresponds to the walking state by analyzing the detected PPG signal.

For example, when the exercise amount of the user corresponds to the running state, the pulse measurement device may detect the PPG signal using the PPG sensor. The pressure applied to the PPG sensor may be controlled to be the excessive pressure, greater than the optimum pressure range. The pulse measurement device further may measure the pulse when the exercise amount of the user corresponds to the running state by analyzing the PPG signal detected by the PPG sensor, whose amount of light is increased.

As described above, in the pulse measurement method, according to one or more embodiments of the present invention, the pressure applied to the PPG sensor or the amount of light of the PPG sensor may be controlled to an optimum condition, according to the exercise amount of the user. The optimum PPG signal detected by the PPG sensor may be analyzed in the described controlled condition, thereby more precisely measuring the pulse of the user.

In operation 1190, the pulse measurement device may determine whether the user finishes exercising by analyzing the acceleration signal detected by the acceleration sensor. The pulse measurement device may also determine whether the pulse measurement feature using the PPG signal is still desired by the user.

When the user does not finish the exercise, or the pulse measurement is still desired, the pulse measurement device may continuously measure the pulse of the user by detecting the PPG signal according to the exercise amount of the user, and may analyze the detected PPG signal via the described operations from operation 1140.

When the user finishes the exercise, or the pulse measurement is completed, the pulse measurement device may complete the operations of the pulse measurement method, according to one or more embodiments of the present invention.

As described above, in the pulse measurement method, according to one or more embodiments of the present invention, a PPG signal may be stably detected by controlling the pressure applied to a PPG sensor according to an exercise amount of a user, and a pulse may be more precisely measured by using the detected PPG signal.

In addition to this discussion, embodiments of the present invention can also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code can be recorded/transferred on a medium in a variety of ways, with examples of the medium including magnetic storage media (e.g., ROM, floppy disks, hard disks, etc.), optical recording media (e.g., CD-ROMs, or DVDs), and storage/transmission media such as carrier waves, as well as through the Internet, for example. Here, the medium may further be a signal, such as a resultant signal or bitstream, according to embodiments of the present invention. The media may also be a distributed network, so that the computer readable code is stored/transferred and executed in a distributed fashion. Still further, as only a example, the processing element could include a processor or a computer processor, and processing elements may be distributed and/or included in a single device.

According to an aspect of one or more embodiments of the present invention, since an optimum PPG measurement pressure suitable for a user may be provided to reduce individual error, a user's pulse may be more precisely measured by detecting an optimum PPG signal.

An aspect of one or more embodiments of the present invention provides a device, method and medium of more precisely measuring a user's pulse by detecting a PPG signal by automatically controlling pressure applied to a PPG sensor according to an exercise amount of the user.

An aspect of one or more embodiments of the present invention also provides a device, method and medium of more precisely measuring a pulse by preventing a maximum peak value of a PPG signal from being reduced. This may be accomplished by increasing an amount of light generated by a PPG sensor when excessive pressure over an optimum pressure range is applied to the PPG sensor to stabilize a measurement position of the PPG sensor when a user exercises heavily.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A pulse measurement device, comprising:
   a sensing unit to sense a photoplethysmography (PPG) signal and to directly sense an acceleration signal obtained from a user;
   a pressure control unit to control pressure applied to the sensing unit;
   a light amount control unit to control an amount of incident light on the sensing unit; and
   a signal determination unit to determine an optimum pressure range by analyzing the PPG signal varying with a change of the pressure applied to the sensing unit by the pressure control unit and to determine an exercise level of an activity of the user by using the acceleration signal,
   wherein the optimal pressure range corresponds to a range of maximum peak values of the PPG signal which have a value greater than a preset percentage of a maximum value among the maximum peak values of the PPG signal,
   wherein the optimal pressure range is a range of pressure values from a minimum pressure value to a maximum pressure value, in which external pressure is applied in accordance with the user's exercise level, the minimum pressure value corresponds to a first maximum peak value of the PPG signal having a value corresponding to the preset percentage of the maximum value among the maximum peak values, and the maximum pressure value corresponds to a second maximum peak value of the PPG signal having a value corresponding to the preset percentage of the maximum value among the maximum peak values, and when the exercise level is determined by the signal determination unit as corresponding to a relatively high level of activity, the pressure control unit controls the pressure applied to the sensing unit to exceed the optimum pressure range and the light amount control unit controls the amount of incident light on the sensing unit to be increased to compensate for any decrease in the PPG signal due to the pressure control unit controlling the pressure to exceed the optimum pressure range.

2. The device of claim 1, wherein the pressure control unit controls the pressure applied to the sensing unit to be the minimum pressure of the optimum pressure range when the exercise level corresponds to a rest state.

3. The device of claim 2, wherein the pressure control unit controls the pressure applied to the sensing unit to be the maximum pressure of the optimum pressure range when the exercise level corresponds to a light walking state.

4. The device of claim 1, wherein the light amount control unit selectively controls the amount of incident light applied to the sensing unit by only increasing the incident light when the exercise level is determined to be a relatively high level of activity and the pressure applied to the sensing unit exceeds the optimum pressure range.

5. A pulse measurement device, comprising:
a sensing unit to sense a photoplethysmography (PPG) signal and an acceleration signal obtained from a user;
a pressure control unit to control pressure applied to the sensing unit;
a light amount control unit to control an amount of incident light on the sensing unit; and
a signal determination unit to determine an optimum pressure range to be applied to the sensing unit by analyzing the PPG signal varying with a change of the pressure applied to the sensing unit by the pressure control unit and to determine an exercise level of an activity of the user by using the acceleration signal,
wherein the light amount control unit selectively controls the amount of incident light applied to the sensing unit by increasing the incident light according to different exercise levels, and
wherein when the exercise level corresponds to a relatively high level of activity, the pressure control unit controls the pressure applied to the sensing unit to exceed the optimum pressure range and the light amount control unit controls the amount of incident light on the sensing unit to be increased to compensate for any decrease in the PPG signal due to the increased pressure by the pressure control unit.

6. A pulse measurement method, comprising:
establishing an optimum pressure range of a photoplethysmography (PPG) sensor by changing pressure applied to the PPG sensor and analyzing a PPG signal detected by the PPG sensor;
measuring an exercise level of a user by analyzing an acceleration signal directly detected by an acceleration sensor;
controlling the pressure applied to the PPG sensor based on the optimum pressure range according to the exercise level of the user; and
measuring a pulse by analyzing the PPG signal detected by the PPG sensor to which the controlled pressure is given,
wherein the optimal pressure range corresponds to a range of maximum peak values of the PPG signal which have a value greater than a preset percentage of a maximum value among the maximum peak values of the PPG signal,
wherein the optimal pressure range is a range of pressure values from a minimum pressure value to a maximum pressure value, in which external pressure is applied in accordance with the user's exercise level, the minimum pressure value corresponds to a first maximum peak value of the PPG signal having a value corresponding to the preset percentage of the maximum value among the maximum peak values, and the maximum pressure value corresponds to a second maximum peak value of the PPG signal having a value corresponding to the preset percentage of the maximum value among the maximum peak values, and
when the exercise level is measured as corresponding to a relatively high level of activity, controlling the pressure applied to the PPG sensor to exceed the optimum pressure range and increasing an amount of incident light on the PPG sensor to compensate for any decrease in the PPG signal due to the controlling of the pressure to exceed the optimum pressure range.

7. The method of claim 6, wherein, in the establishing an optimum pressure range of a PPG sensor by changing pressure applied to the PPG sensor and analyzing a PPG signal detected by the PPG sensor,
the PPG signal detected by the PPG sensor is analyzed by increasing the pressure applied to the PPG sensor.

8. The method of claim 6, wherein, in the controlling the pressure applied to the PPG sensor based on the optimum pressure range according to the exercise level of the user,
when the exercise level of the user is corresponding to a rest state, the pressure applied to the PPG sensor is controlled to be the minimum pressure of the optimum pressure range.

9. The method of claim 8, wherein, in the controlling the pressure applied to the PPG sensor based on the optimum pressure range according to the exercise level of the user,
when the exercise amount of the user is corresponding to a walking state, the pressure applied to the PPG sensor is controlled to be the maximum pressure of the optimum pressure range.

10. A non-transitory medium comprising computer readable code to control at least one processing element to implement a pulse measurement method, the method comprising:
establishing an optimum pressure range of a photoplethysmography (PPG) sensor by changing pressure applied to the PPG sensor and analyzing a PPG signal detected by the PPG sensor;
measuring an exercise level of a user by analyzing an acceleration signal directly detected by an acceleration sensor;
controlling the pressure applied to the PPG sensor based on the optimum pressure range according to the exercise level of the user; and
measuring a pulse by analyzing the PPG signal detected by the PPG sensor to which the controlled pressure is given,
wherein the optimal pressure range corresponds to a range of maximum peak values of the PPG signal which have a value greater than a preset percentage of a maximum value among the maximum peak values of the PPG signal,
wherein the optimal pressure range is a range of pressure values from a minimum pressure value to a maximum pressure value, in which external pressure is applied in accordance with the user's exercise level, the minimum pressure value corresponds to a first maximum peak value of the PPG signal having a value corresponding to the preset percentage of the maximum value among the maximum peak values, and the maximum pressure value corresponds to a second maximum peak value of the PPG signal having a value corresponding to the preset percentage of the maximum value among the maximum peak values, and when the exercise level is measured as corresponding to a relatively high level of activity, controlling the pressure applied to the PPG sensor to exceed the optimum pressure range and increasing an amount of incident light on the PPG sensor to compensate for any decrease in the PPG signal due to the controlling of the pressure to exceed the optimum pressure range.

11. The method of claim 6, further comprising selectively controlling an amount of incident light applied to the PPG sensor by increasing the incident light according to different exercise levels of the user.

* * * * *